United States Patent
Mutnury et al.

(10) Patent No.: US 10,126,110 B2
(45) Date of Patent: Nov. 13, 2018

(54) SYSTEMS AND METHODS FOR FREQUENCY SHIFTING RESONANCE OF AN UNUSED VIA IN A PRINTED CIRCUIT BOARD

(71) Applicant: Dell Products L.P., Round Rock, TX (US)

(72) Inventors: Bhyrav M. Mutnury, Round Rock, TX (US); Sandor Farkas, Round Rock, TX (US); Stuart Allen Berke, Austin, TX (US)

(73) Assignee: Dell Products L.P., Round Rock, TX (US)

( * ) Notice: Subject to any disclaimer, the term of this patent is extended or adjusted under 35 U.S.C. 154(b) by 712 days.

(21) Appl. No.: 14/677,678

(22) Filed: Apr. 2, 2015

(65) Prior Publication Data

US 2015/0211837 A1 Jul. 30, 2015

Related U.S. Application Data

(63) Continuation of application No. 13/778,941, filed on Feb. 27, 2013, now Pat. No. 9,024,208.

(51) Int. Cl.
| | |
|---|---|
| *H05K 1/11* | (2006.01) |
| *G01B 7/02* | (2006.01) |
| *H05K 3/00* | (2006.01) |
| *H05K 3/42* | (2006.01) |
| *H05K 1/02* | (2006.01) |
| *G01N 27/02* | (2006.01) |
| *H05K 3/46* | (2006.01) |

(52) U.S. Cl.
CPC ............... *G01B 7/02* (2013.01); *G01N 27/02* (2013.01); *H05K 1/0251* (2013.01); *H05K 1/0298* (2013.01); *H05K 1/113* (2013.01); *H05K 1/115* (2013.01); *H05K 3/0094* (2013.01); *H05K 3/429* (2013.01); *H05K 3/46* (2013.01); *H05K 2201/094* (2013.01); *H05K 2201/09454* (2013.01); *Y10T 29/49155* (2015.01); *Y10T 29/49165* (2015.01)

(58) Field of Classification Search
CPC ............... H05K 1/0231; H05K 1/0251; H05K 2201/0949; H05K 3/429; H05K 1/112; H05K 1/113; H05K 1/115; H05K 1/116
USPC .................................................. 174/262–266
See application file for complete search history.

(56) References Cited

U.S. PATENT DOCUMENTS

| | | | |
|---|---|---|---|
| 2002/0084105 A1 | 7/2002 | Geng et al. | |
| 2003/0178229 A1* | 9/2003 | Toyoda ................. | H01L 21/486 174/261 |

(Continued)

*Primary Examiner* — Steven T Sawyer
(74) *Attorney, Agent, or Firm* — Jackson Walker L.L.P.

(57) ABSTRACT

In accordance with embodiments of the present disclosure, a circuit board may include a first trace formed in a first layer of the circuit board, a second trace formed in a second layer of the circuit board, a via, and a termination pad. The via may be configured to electrically couple the first trace to the second trace, the via comprising a via stub corresponding to a first portion of a length of the via not within a second portion of the via between a first location in which the first trace is electrically coupled to the via and a second location in which the second trace is electrically coupled to the via. The termination pad may be formed at an end of the via stub opposite at least one of the first location and the second location.

16 Claims, 3 Drawing Sheets

(56) References Cited

U.S. PATENT DOCUMENTS

| | | |
|---|---|---|
| 2004/0176938 A1 | 9/2004 | Gisin et al. |
| 2005/0190614 A1 | 9/2005 | Brunette et al. |
| 2006/0284310 A1 | 12/2006 | Hall et al. |
| 2007/0023913 A1* | 2/2007 | Audet .................. H01L 21/486 |
| | | 257/751 |
| 2007/0074905 A1* | 4/2007 | Lin .................... G06F 17/5068 |
| | | 174/263 |
| 2007/0091581 A1* | 4/2007 | Gisin .................... H05K 1/023 |
| | | 361/782 |
| 2007/0103251 A1 | 5/2007 | Fan et al. |
| 2007/0132527 A1* | 6/2007 | Chen ........................ H03H 7/38 |
| | | 333/33 |
| 2008/0191362 A1 | 8/2008 | Chuang et al. |
| 2009/0049414 A1 | 2/2009 | Mutnury et al. |
| 2009/0159326 A1 | 6/2009 | Mellitz |
| 2009/0294168 A1 | 12/2009 | Pai et al. |
| 2010/0319979 A1* | 12/2010 | Hsu ..................... H05K 1/0251 |
| | | 174/262 |

* cited by examiner

SYSTEMS AND METHODS FOR FREQUENCY SHIFTING RESONANCE OF AN UNUSED VIA IN A PRINTED CIRCUIT BOARD

The present patent application is a continuation of a previously filed patent application, U.S. patent application Ser. No. 13/778,941, filed Feb. 27, 2013, the entirety of which is hereby incorporated by reference.

TECHNICAL FIELD

The present disclosure relates in general to information handling systems, and more particularly to a system and method for frequency shifting resonance of an unused via stub in a printed circuit board.

BACKGROUND

As the value and use of information continues to increase, individuals and businesses seek additional ways to process and store information. One option available to users is information handling systems. An information handling system generally processes, compiles, stores, and/or communicates information or data for business, personal, or other purposes thereby allowing users to take advantage of the value of the information. Because technology and information handling needs and requirements vary between different users or applications, information handling systems may also vary regarding what information is handled, how the information is handled, how much information is processed, stored, or communicated, and how quickly and efficiently the information may be processed, stored, or communicated. The variations in information handling systems allow for information handling systems to be general or configured for a specific user or specific use such as financial transaction processing, airline reservations, enterprise data storage, or global communications. In addition, information handling systems may include a variety of hardware and software components that may be configured to process, store, and communicate information and may include one or more computer systems, data storage systems, and networking systems.

An information handling system may include one or more circuit boards operable to mechanically support and electrically couple electronic components making up the information handling system. For example, circuit boards may be used as part of motherboards, memories, storage devices, storage device controllers, peripherals, peripheral cards, network interface cards, and/or other electronic components. As is known in the art, a circuit board may comprise a plurality of conductive layers separated and supported by layers of insulating material laminated together, with conductive traces disposed on and/or in any of such conductive layers. As also known in the art, connectivity between conductive traces disposed on and/or in various layers of a circuit board may be provided by conductive vias.

Typically, during manufacturing of a circuit board, each via is formed to approximately the thickness of the circuit board, thus permitting electrical conductivity between traces on the various layers of the circuit board. As a result, a portion of a via may be "unused" in the sense that such portion is present but not needed to conduct a signal between circuit board layers. FIG. 1 depicts a circuit board 10 having a via 6 with an unused portion 8. As shown in FIG. 1, a circuit board 10 may include various layers, including ground planes 2 and signal layers having traces 4 formed therein. Pads 12 formed of substantially conductive material may also be formed in circuit board 10 in order to electrically couple traces 4 to vias 6 as desired. Thus, as can be seen from FIG. 1, a via 6 may have a portion used to create an electrically conductive pathway between traces 4 on different layers of circuit board 10, an unused portion or "stub" 8 which is not part of an electrically conductive path between traces 4.

A via stub 8 may act as an antenna, and thus may resonate at frequencies (and harmonics thereof) for which the length of via stub 8 is equal to one-quarter of the wavelength of such frequencies. As transmission frequencies used in circuit boards increase, signals operating at such frequencies may be affected by such resonances, resulting in decreased signal integrity.

Although various traditional approaches may be employed to mitigate the effect of via stub resonances, such approaches have disadvantages. For example, backdrilling or counter boring may be used in which a mechanical drill is used to remove a part of a via stub 8. However, such process may significantly increase the cost of circuit board manufacture. In addition, due to mechanical tolerances of a drill used to backdrill or counter bore, a small portion of via stub 8 may still remain, and thus some resonance may still occur.

SUMMARY

In accordance with the teachings of the present disclosure, the disadvantages and problems associated with resonance in printed circuit board via stubs have been reduced or eliminated.

In accordance with embodiments of the present disclosure, a circuit board may include a first trace formed in a first layer of the circuit board, a second trace formed in a second layer of the circuit board, a via, and a termination pad. The via may be configured to electrically couple the first trace to the second trace, the via comprising a via stub corresponding to a first portion of a length of the via not within a second portion of the via between a first location in which the first trace is electrically coupled to the via and a second location in which the second trace is electrically coupled to the via. The termination pad may be formed at an end of the via stub opposite at least one of the first location and the second location.

In accordance with these and other embodiments of the present disclosure, an information handling system may include a circuit board and at least one information handling resource other than the circuit board. The circuit board may include a first trace formed in a first layer of the circuit board, a second trace formed in a second layer of the circuit board, a via, and a termination pad. The via may be configured to electrically couple the first trace to the second trace, the via comprising a via stub corresponding to a first portion of a length of the via not within a second portion of the via between a first location in which the first trace is electrically coupled to the via and a second location in which the second trace is electrically coupled to the via. The termination pad may be formed at an end of the via stub opposite at least one of the first location and the second location.

In accordance with these and other embodiments of the present disclosure, a method may include determining a length of a via stub, the via stub corresponding to a first portion of a via not within a second portion of the via electrically coupling a first trace of a circuit board to a second trace of the circuit board. The method may also include determining a Nyquist frequency of signals communicated on the via and one or more harmonic frequencies thereof. The method may additionally include estimating a resonance frequency of the via stub based on the length. The method may further include determine a size of a termination pad to be formed on an end of the via stub in response to determining that the resonance frequency is approximately equal to the Nyquist frequency or one of the one or more harmonic frequencies.

Technical advantages of the present disclosure will be apparent to those of ordinary skill in the art in view of the following specification, claims, and drawings.

BRIEF DESCRIPTION OF THE DRAWINGS

A more complete understanding of the present embodiments and advantages thereof may be acquired by referring to the following description taken in conjunction with the accompanying drawings, in which like reference numbers indicate like features, and wherein.

DETAILED DESCRIPTION

Figure 1:
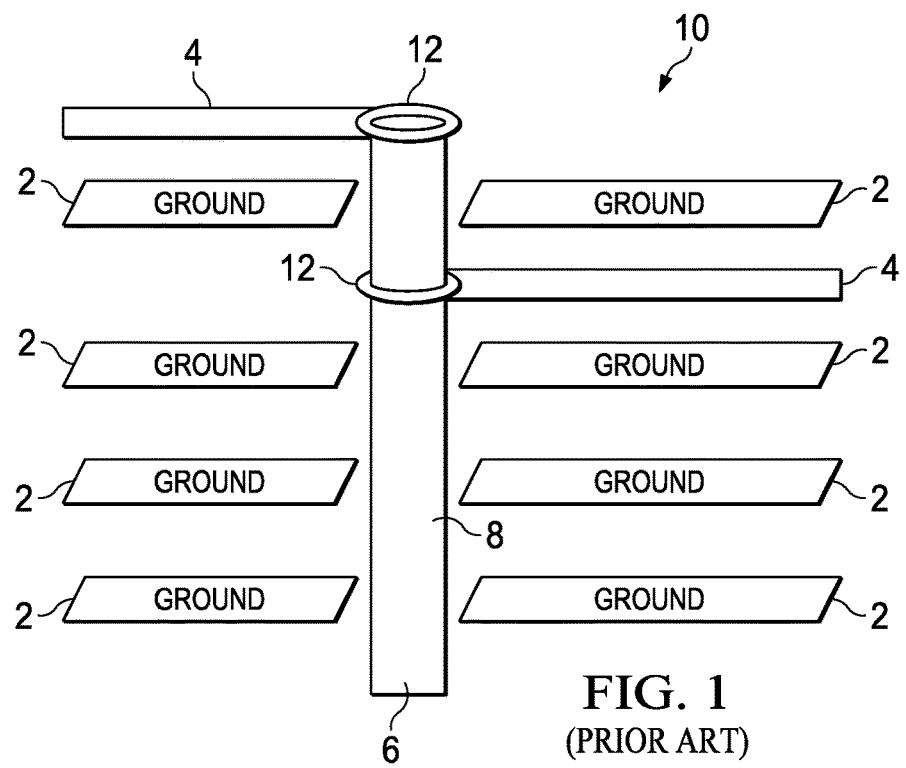
FIG. 1 illustrates an elevation view of selected components of a printed circuit board, as is known in the art.

Preferred embodiments and their advantages are best understood by reference to FIGS. 2 through 6, wherein like numbers are used to indicate like and corresponding parts.

For purposes of this disclosure, an information handling system may include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, or other purposes. For example, an information handling system may be a personal computer, a network storage device, or any other suitable device and may vary in size, shape, performance, functionality, and price. The information handling system may include random access memory (RAM), one or more processing resources such as a central processing unit (CPU) or hardware or software control logic, ROM, and/or other types of nonvolatile memory. Additional components of the information handling system may include one or more disk drives, one or more network ports for communicating with external devices as well as various input and output (I/O) devices, such as a keyboard, a mouse, and a video display. The information handling system may also include one or more buses operable to transmit communications between the various hardware components.

For the purposes of this disclosure, computer-readable media may include any instrumentality or aggregation of instrumentalities that may retain data and/or instructions for a period of time. Computer-readable media may include, without limitation, storage media such as a direct access storage device (e.g., a hard disk drive or floppy disk), a sequential access storage device (e.g., a tape disk drive), compact disk, CD-ROM, DVD, random access memory (RAM), read-only memory (ROM), electrically erasable programmable read-only memory (EEPROM), and/or flash memory; as well as communications media such as wires, optical fibers, microwaves, radio waves, and other electromagnetic and/or optical carriers; and/or any combination of the foregoing.

For the purposes of this disclosure, information handling resources may broadly refer to any component system, device or apparatus of an information handling system, including without limitation processors, service processors, basic input/output systems, buses, memories, I/O devices and/or interfaces, storage resources, network interfaces, motherboards, and/or any other components and/or elements of an information handling system.

As discussed above, an information handling system may include one or more circuit boards operable to mechanically support and electrically connect electronic components making up the information handling system (e.g., packaged integrated circuits). Circuit boards may be used as part of motherboards, memories, storage devices, storage device controllers, peripherals, peripheral cards, network interface cards, and/or other electronic components. As used herein, the term "circuit board" includes printed circuit boards (PCBs), printed wiring boards (PWBs), etched wiring boards, and/or any other board or similar physical structure operable to mechanically support and electrically couple electronic components.

Figure 2:
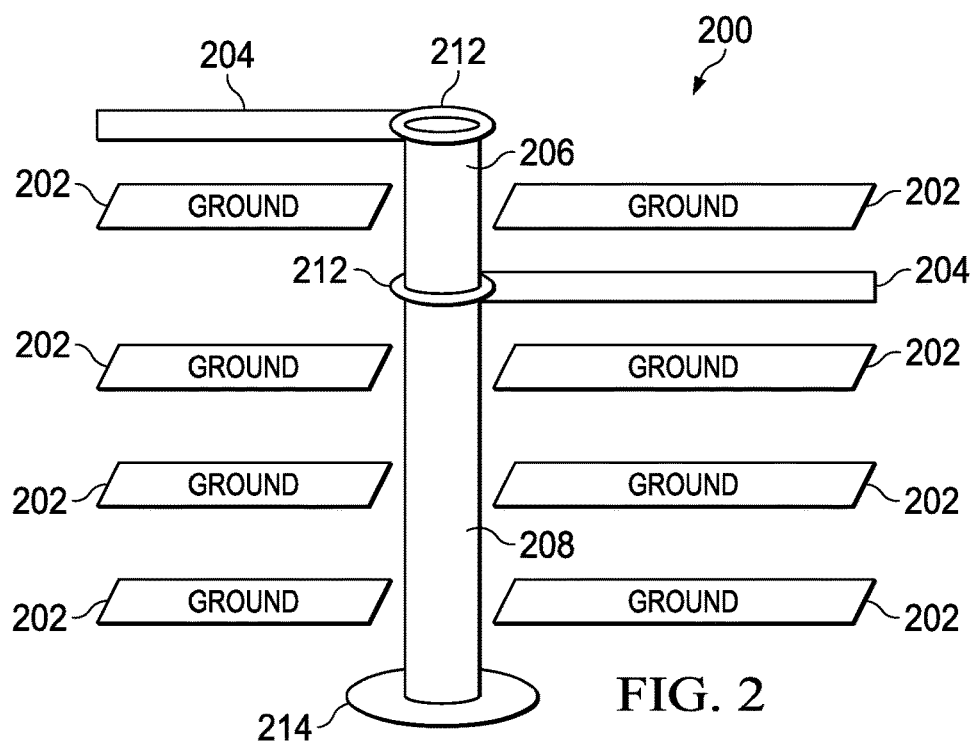
FIG. 2 illustrates an elevation view of selected components of a printed circuit board, in accordance with embodiments of the present disclosure.

FIG. 2 illustrates an elevation view of selected components of a circuit board 200, in accordance with embodiments of the present disclosure. As shown in FIG. 2, circuit board 200 may include various layers, including ground planes 202 and signal layers having traces 204 formed therein. A ground plane 202 may comprise a large area of substantially electrically conductive material coupled to circuit board 200's ground point, usually one terminal of a power supply, and may serve as a return path for current from many different components. A ground plane 202 is often made as large as possible, covering most of the area of the circuit board layer which is not occupied by circuit traces 204 or vias 206. In multilayer circuit boards, a ground plane may be implemented as a whole layer of substantially electrically conductive material, except for portions of the layer through which vias 206 may pass.

A trace 204 may comprise a substantially electrically conductive material and may be formed on a surface of circuit board 200, or in a layer of circuit board 200 not visible from the surface thereof.

Circuit board 200 may also comprise one or more vias 206. A via 206 may comprise a substantially electrically conductive material and may be formed such that via 206 may electrically couple together traces 204 on different layers of circuit board 200, thus allowing signals to propagate between layers of circuit board 200. In some embodiments, via 206 may be substantially cylindrical in shape.

Circuit board 200 may additionally include pads 212. Each pad 212 may be formed of substantially electrically conductive material and may also be formed in circuit board 200 in order to electrically couple traces 204 to vias 206 in accordance with the design and/or architecture of circuit board 200. In some embodiments, a pad 212 may be substantially disc-shaped (e.g., a cylinder with a height much less than that of its radius) with a similar concentric disc-shaped hole to allow passage of via 206.

As described in the "Background" section and as shown in FIG. 2, a portion of via 206 may comprise a via stub 208 that extends beyond pads 212 coupling via 206 to traces 204 and is thus not used to conduct electric current (e.g., electronic signals) between traces 204. In accordance with this disclosure, such via stub 208 may be terminated by a termination pad 214 at an end of via stub 208. In some embodiments, a termination pad 214 may be substantially disc-shaped (e.g., a cylinder with a height much less than that of its radius) with a similar concentric disc-shaped hole to allow passage of via 206. Such termination pad 214 may, as compared to an unterminated via stub 208, increase an effective impedance (e.g., capacitance and/or inductance) of via stub 208. Such increased impedance may have the effect of increasing the resonant frequency of via stub 208. Accordingly, such a termination pad 214 may be added to "shift" a resonant frequency of via stub 208 to a frequency that minimally interferes with signals communicated through via 206 at a communication frequency.

Figure 3:
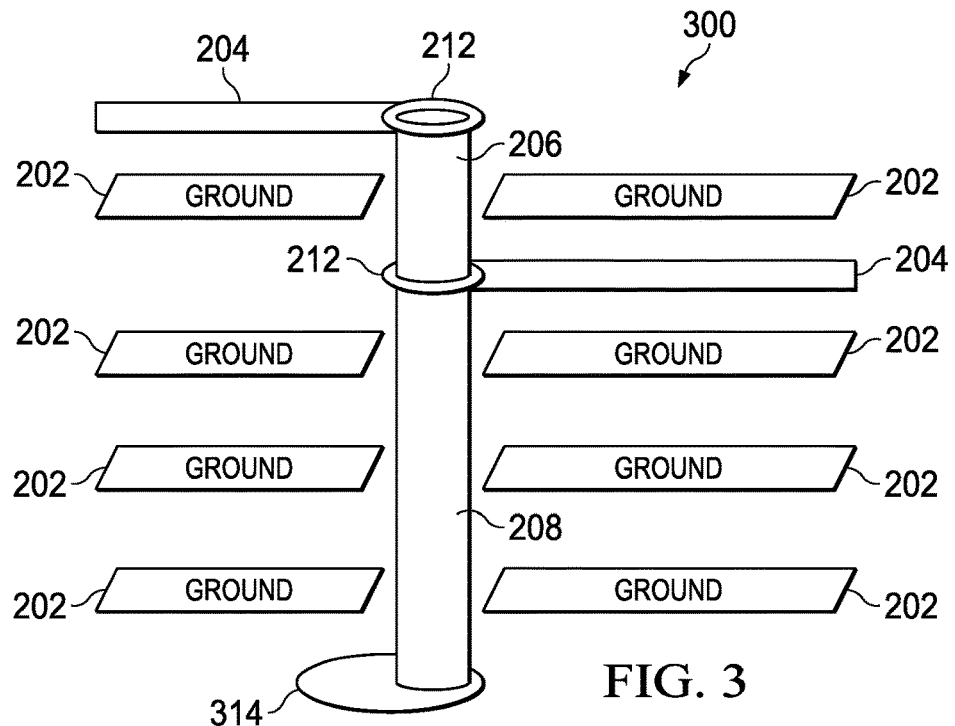
FIG. 3 illustrates an elevation view of selected components of another printed circuit board, in accordance with embodiments of the present disclosure.

Although FIG. 2 depicts a termination pad 214 that is substantially concentric with the via 206 it terminates, in some embodiments, for example the embodiments represented by FIG. 3, the center of a termination pad 314 may be offset from the center of via 206, thus creating an effective inductance which is a function of the degree of offset. Such inductance may also increase the resonant frequency of via stub 208, also permitting a shift of the resonant frequency of via stub 208 to a frequency that minimally interferes with signals communicated through via 206 at a communication frequency.

Figure 4:
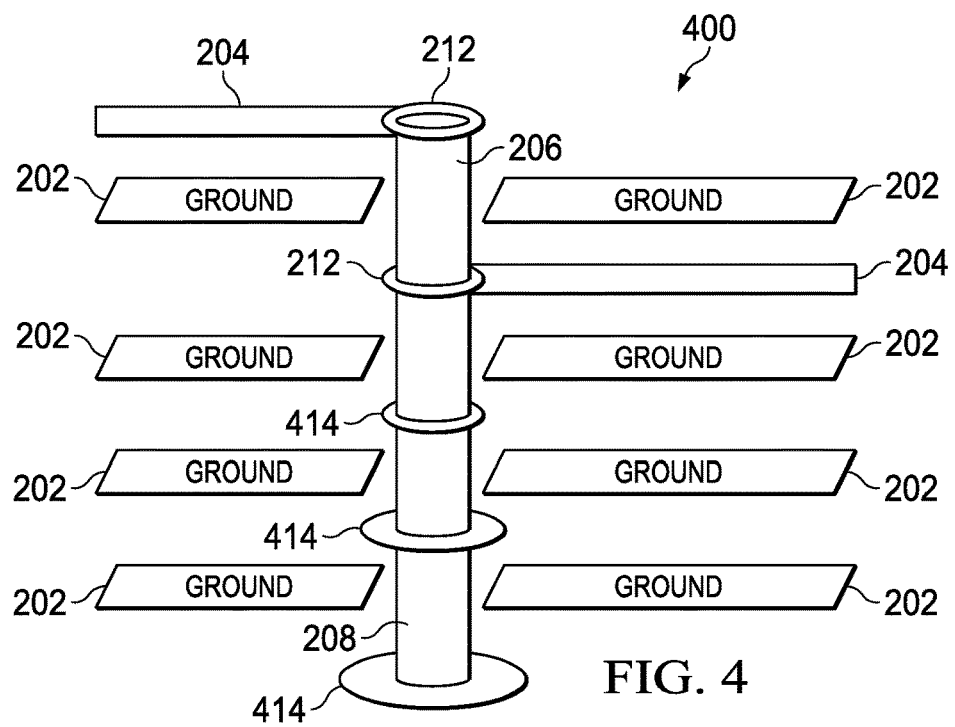
FIG. 4 illustrates an elevation view of selected components of yet another printed circuit board, in accordance with embodiments of the present disclosure.

In addition, although FIGS. 2 and 3 depict a termination pad 214 or 314 at an end of via stub 208, in some embodiments, for example the embodiments represented by FIG. 4, a termination pad 414 may be formed not only at the end of via stub 208, but also at one or more signal layers along the length of via stub 208. In some embodiments, the size of such termination pads 414 may decrease from the end of via stub 208 to a pad 212 coupling a trace 204 to via 206, as is also shown in FIG. 4. In some of such embodiments, the difference in sizes between successive termination pads 414 may be equal to a pre-defined ratio. As in FIGS. 2 and 3, the presence of termination pads 414 may increase the effective impedance of via stub 208. However, the plurality of termination pads 414 along the length of via stub 208 may be particularly suited for narrowband applications, as the plurality of termination pads may result in impedance discontinuities that resonate at frequent intervals, thus acting like a narrowband filter.

The various ground planes 202, traces 204, vias 206, and termination pads 214, 314, and 414 may comprise silver, copper, aluminum, lead, nickel, other metals, metal alloys, and/or any other conductive material that may readily conduct electrical current.

Figure 5:
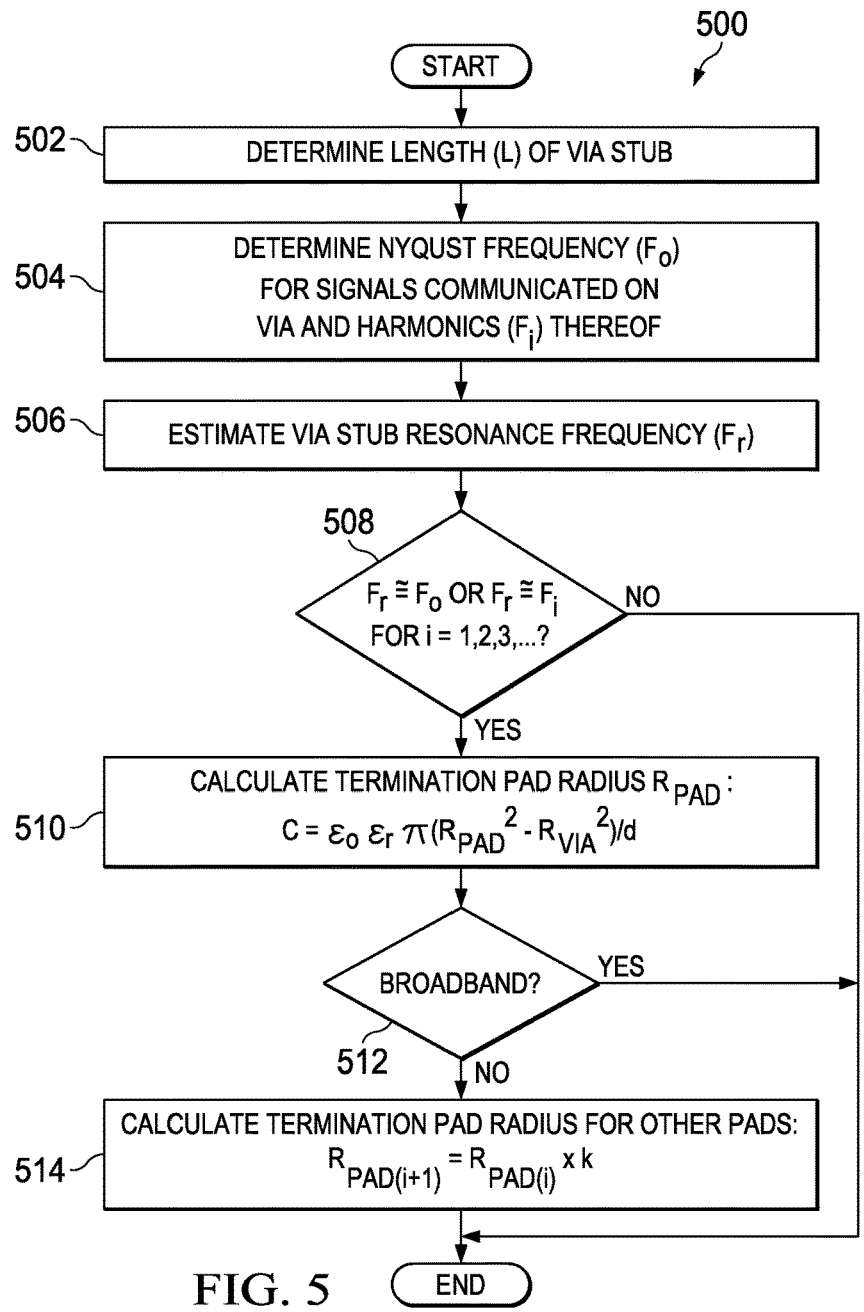
FIG. 5 illustrates a flow chart of an example method for determining a via stub pad termination size, in accordance with embodiments of the present disclosure.

FIG. 5 illustrates a flow chart of an example method 500 for determining a via stub pad termination size, in accordance with embodiments of the present disclosure. According to some embodiments, method 500 preferably begins at step 502. As noted above, teachings of the present disclosure may be implemented in a variety of configurations of circuit boards 200, 300 and 400. As such, the preferred initialization point for method 500 and the order of the steps comprising method 500 may depend on the implementation chosen.

At step 502, a length (L) of a via stub (e.g., via stub 208) may be determined. In addition, at step 504, a Nyquist frequency ($F_0$) may be calculated for the sampling rate of signals to be transmitted on a circuit including the via having the via stub, in addition to harmonics ($F_i$) of the Nyquist frequency, which may be integer multiples of the Nyquist frequency.

At step 506, based on the length L of the via stub, a resonance frequency ($F_r$) of the via stub may be estimated. For example, such estimate may be made in accordance with the equation $F_r=1/(4Lt_{prop})$, where $t_{prop}$ equals the propagation time per unit length of a signal through the via stub.

At step 508, a determination may be made whether the resonance frequency $F_r$ is approximately equal (e.g., within a pre-defined tolerance of) the Nyquist frequency $F_0$ or any of the harmonic frequencies $F_i$, thus indicating potential interference of signals by the via stub resonance. If the resonance frequency is approximately equal to the Nyquist frequency or any of the harmonic frequencies, method 500 may proceed to step 510. Otherwise, method 500 may end.

At step 510, a size for a termination pad (e.g., termination pad 214, 314, 414) to be formed at the end of the via stub may be calculated. In some embodiments, such size may be defined by a radius $R_{PAD}$ which is defined by the equation $C=\varepsilon_o\varepsilon_r\pi(R_{PAD}^2-R_{VIA}^2)/d$ where C is a desired capacitance for the termination pad, $\varepsilon_o$ is the permittivity of free space (approximately $8.854187817\times10^{-12}$ farads per meter), $\varepsilon_r$ is the relative permittivity of the material between the termination pad and the most proximate ground plane (e.g., a ground plane 202) of the circuit board, $\pi$ is a mathematical constant that is the ratio of a circle's circumference to its diameter, $R_{VIA}$ is the radius of the via, and d is the dielectric distance between the termination pad and the most proximate ground plane.

At step 512, a determination may be made whether the signal path including the via is narrowband or broadband. If broadband, method 500 may end. If narrowband, method 500 may proceed to step 514.

At step 514, sizes for additional termination pads to be formed at one or more signal layers along the length of the via stub may be calculated. In some embodiments, such pad size may be calculated in accordance with the formula $R_{PAD(i)}=KR^{PAD(i-1)}$, for i=1 to N, where N equals the number of termination pads to be formed at one or more signal layers along the length of the via stub, K equals a predefined dimensionless constant, and $R_{PAD(0)}$ equals the value of $R_{PAD}$ calculated in accordance with step 510. After completion of step 514, method 500 may end.

Although FIG. 5 discloses a particular number of steps to be taken with respect to method 500, method 200 may be executed with greater or lesser steps than those depicted in FIG. 5. In addition, although FIG. 5 discloses a certain order of steps to be taken with respect to method 500, the steps comprising method 500 may be completed in any suitable order.

Method 500 may be implemented using any system operable to implement method 500. In certain embodiments, method 500 may be implemented partially or fully in software and/or firmware embodied in computer-readable media. In these and other embodiments, method 500 may be performed by an information handling system, for example information handling system 600 depicted in FIG. 6.

In some embodiments, method 500 may also include offsetting the center of a termination pad from the center of a via in order to create a desired effective inductance for the via stub.

Figure 6:
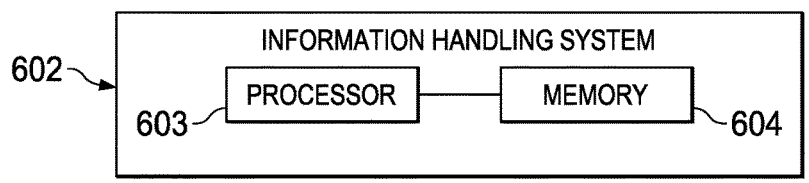
FIG. 6 illustrates a block diagram of an example information handling system, in accordance with certain embodiments of the present disclosure.

FIG. 6 illustrates a block diagram of an example information handling system 602, in accordance with certain embodiments of the present disclosure. As depicted in FIG.

6, information handling system 602 may include a processor 603 and a memory 604 communicatively coupled to processor 603.

Processor 603 may include any system, device, or apparatus configured to interpret and/or execute program instructions and/or process data, and may include, without limitation, a microprocessor, microcontroller, digital signal processor (DSP), application specific integrated circuit (ASIC), or any other digital or analog circuitry configured to interpret and/or execute program instructions and/or process data. In some embodiments, processor 603 may interpret and/or execute program instructions and/or process data stored in memory 604 and/or another information handling resource of information handling system 602.

Memory 604 may be communicatively coupled to processor 603 and may include any system, device, or apparatus configured to retain program instructions and/or data for a period of time (e.g., computer-readable media). Memory 604 may include RAM, EEPROM, a PCMCIA card, flash memory, magnetic storage, opto-magnetic storage, or any suitable selection and/or array of volatile or non-volatile memory that retains data after power to information handling system 602 is turned off. In some embodiments, memory 604 may have stored thereon a program of instructions that when read and executed by processor 603, carries out method 500 described above.

In addition to processor 603 and memory 604, information handling system 602 may include one or more other information handling resources.

Although the present disclosure has been described in detail, it should be understood that various changes, substitutions, and alterations can be made hereto without departing from the spirit and the scope of the disclosure as defined by the appended claims.

What is claimed is:

1. A circuit board, comprising:
a plurality of layers including at least a first layer and a second layer;
a first trace formed in the first layer of the circuit board;
a second trace formed in the second layer of the circuit board;
a via configured to electrically couple the first trace to the second trace, wherein the via is coupled to the first trace at a first location and coupled to the second trace at a second location, the via comprising a via stub that is not located between the first layer and the second layer and is not operable to conduct signals among the plurality of layers;
a first termination pad formed at an end of the via stub opposite at least one of the first location and the second location, wherein the first termination pad is offset from a center axis of the via stub; and
one or more second termination pads formed at one or more layers of the circuit board other than the first layer and the second layer, wherein the one or more second termination pads are smaller in size than the first termination pad;
wherein the first termination pad and the one or more second termination pads are not operable to couple the via to any traces.

2. The circuit board of claim 1, the first termination pad formed such that an effective impedance of the via stub is approximately equal to a desired impedance.

3. The circuit board of claim 2, the first termination pad and the one or more second termination pads each formed with a respective size such that the effective impedance of the via stub is approximately equal to the desired impedance.

4. The circuit board of claim 3, wherein the respective sizes are radii of the first termination pad and the one or more second termination pads.

5. The circuit board of claim 2, wherein the desired impedance comprises at least one of a desired capacitance and a desired inductance.

6. The circuit board of claim 2, wherein the desired impedance is selected such that the via stub has a desired effective resonant frequency.

7. A method, comprising:
forming a plurality of layers including at least a first layer and a second layer in a circuit board;
forming a first trace in the first layer of a circuit board;
forming a second trace in the second layer of the circuit board;
electrically coupling the first trace to the second trace with a via, wherein the via is coupled to the first trace at a first location and coupled to the second trace at a second location, the via comprising a via stub that is not located between the first layer and the second layer and is not operable to conduct signals among the plurality of layers;
forming a first termination pad at an end of the via stub opposite at least one of the first location and the second location, wherein the first termination pad is offset from a center axis of the via stub; and
forming one or more second termination pads at one or more layers of the circuit board other than the first layer and the second layer, wherein the one or more second termination pads are smaller in size than the first termination pad;
wherein the first termination pad and the one or more second termination pads are not operable to couple the via to any traces.

8. The method of claim 7, wherein forming the first termination pad comprises forming the termination pad such that an effective impedance of the via stub is approximately equal to a desired impedance.

9. The method of claim 8, wherein forming the first termination pad and forming the one or more second termination pads comprises forming each of the first termination pad and the one or more second termination pads with a respective size such that the effective impedance of the via stub is approximately equal to the desired impedance.

10. The method of claim 9, wherein the respective sizes are radii of the first termination pad and the one or more second termination pads.

11. The method of claim 8, wherein the desired impedance comprises at least one of a desired capacitance and a desired inductance.

12. The method of claim 8, wherein the desired impedance is selected such that the via stub has a desired effective resonant frequency.

13. The method of claim 7, wherein the one or more second termination pads comprise a plurality of second termination pads, wherein the respective sizes of each second termination pad successfully decrease from the end of the via stub.

14. The method of claim 13, wherein differences in sizes between successive second termination pads are equal to a pre-defined ratio.

15. The circuit board of claim 1, wherein the one or more second termination pads comprise a plurality of second termination pads, wherein the respective sizes of each second termination pad successfully decrease from the end of the via stub.

16. The circuit board of claim 15, wherein differences in sizes between successive second termination pads are equal to a pre-defined ratio.

\* \* \* \* \*